(12) United States Patent
Mitani et al.

(10) Patent No.: US 8,741,859 B2
(45) Date of Patent: Jun. 3, 2014

(54) FUNGICIDE COMPOSITION FOR AGRICULTURE AND HORTICULTURE AND METHOD FOR PREVENTING PLANT DISEASES

(75) Inventors: Shigeru Mitani, Osaka (JP); Koji Sugimoto, Kusatsu (JP); Yasuko Takii, Kusatsu (JP)

(73) Assignee: Ishihara Sangyo Kaisha, Ltd, Osaka (JP)

( * ) Notice: Subject to any disclaimer, the term of this patent is extended or adjusted under 35 U.S.C. 154(b) by 0 days.

(21) Appl. No.: 12/934,852

(22) PCT Filed: Mar. 27, 2009

(86) PCT No.: PCT/JP2009/056380
§ 371 (c)(1),
(2), (4) Date: Sep. 27, 2010

(87) PCT Pub. No.: WO2009/119842
PCT Pub. Date: Oct. 1, 2009

(65) Prior Publication Data
US 2011/0028419 A1    Feb. 3, 2011

(30) Foreign Application Priority Data

Mar. 28, 2008  (JP) .................. 2008-085318
May 23, 2008   (JP) .................. 2008-135649

(51) Int. Cl.
*A61K 31/70*    (2006.01)
*A61K 31/415*   (2006.01)
*A61K 31/40*    (2006.01)

(52) U.S. Cl.
USPC ............... 514/43; 514/25; 514/398; 514/412

(58) Field of Classification Search
USPC ...................... 514/25, 43, 398, 412
See application file for complete search history.

(56) References Cited

U.S. PATENT DOCUMENTS 3,625,940 A * 12/1971 Suzuki et al. ............ 536/28.53
2004/0241098 A1  12/2004 Labourdette et al.

FOREIGN PATENT DOCUMENTS

| CN | 88101228 A | 12/1988 |
| CN | 1942442 A | 4/2007 |
| CN | 101060781 A | 10/2007 |
| EP | 0298196 A1 | 1/1989 |
| EP | 1952689 A1 | 8/2008 |
| JP | 42-10941 | 6/1967 |
| JP | 63-99005 A | 4/1988 |
| JP | 1-131163 A | 5/1989 |
| JP | 2007-169265 A | 7/2007 |
| RU | 2 304 388 C2 | 8/2007 |

OTHER PUBLICATIONS

International Search Report (PCT/ISA/210) for PCT/JP2009/056380, dated Apr. 10, 2009.
The State Intellectual Property Office of the People's Republic of China, Office Action dated Nov. 13, 2012, issued in counterpart Chinese Patent Application No. 200980111204.X.
Egyptian Patent Office, Office Action dated May 13, 2013 issued in counterpart Egyptian Application No. 2010091629.
Russian Patent Office, Office Action dated Feb. 5, 2013, issued in counterpart Russian Patent Application No. 2010144047.
State Intellectual Property Office of the People's Republic of China, Office Action dated Aug. 26, 2013, in Chinese Application No. 200980111204.X.

* cited by examiner

*Primary Examiner* — Elli Peselev
(74) *Attorney, Agent, or Firm* — Sughrue Mion, PLLC

(57) ABSTRACT

The present invention provides a composition in which a fungicidal effect against a cultivated crop infected by a plant disease is stable and highly active. An excellent agricultural or horticultural fungicide composition for controlling a plant disease is provided by using (a) at least one imidazole compound represented by formula (I):

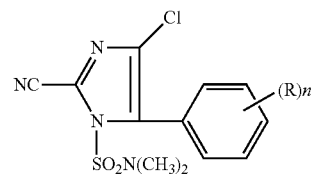

wherein R represents a $C_{1-6}$ alkyl group or a $C_{1-6}$ alkoxy group; and n represents an integer of 1 to 5 and (b) polyoxins as active ingredients; by combination as compared to a single use of each compound, and a plant disease is thereby controlled.

7 Claims, No Drawings

FUNGICIDE COMPOSITION FOR AGRICULTURE AND HORTICULTURE AND METHOD FOR PREVENTING PLANT DISEASES

TECHNICAL FIELD

The present invention relates to an agricultural or horticultural fungicide composition having a markedly improved control effect against a plant disease, especially preventive and/or therapeutic effect against a plant disease; and a method for controlling a plant disease using thereof.

BACKGROUND ART

Patent Literature 1 discloses that an imidazole compound, one of the active ingredients in the agricultural or horticultural fungicide composition of the present invention, is useful as a harmful bio-organism controlling agent. In addition, it also discloses that if necessary, the imidazole compound can be mixed with or used in combination with other fungicides. Furthermore, Patent Literature 2 discloses polyoxins as antibiotics. However, these literatures do not disclose the combination of active-ingredient compounds in the agricultural or horticultural fungicide composition of the present invention.

CITATION LIST

Patent Literature

Patent Literature 1 EP-A-298196
Patent Literature 2 JP-B-42-10941

SUMMARY OF INVENTION

Technical Problem

Since each imidazole compound represented by the following formula (I) is slightly insufficient in a control effect against specific plant diseases or is relatively short in residual efficacy in some cases, it practically exhibits only an insufficient control effect against a plant disease in some conditions for application.

Solution to Problem

As a result of investigations to solve the above-described problem, the present inventors have found that use of an imidazole compound represented by the following formula (I) in combination with polyoxins exhibits an unpredictable and more excellent control effect against a plant disease as compared to a single use of each compound, and have completed the present invention.

That is, the present invention relates to an agricultural or horticultural fungicide composition comprising (a) at least one imidazole compound represented by formula (I):

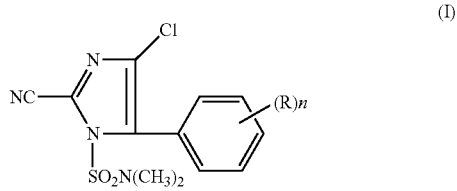

(I)

wherein R represents a $C_{1-6}$ alkyl group or a $C_{1-6}$ alkoxy group; and n represents an integer of 1 to 5, and (b) polyoxins as active ingredients. Also, the present invention relates to a method for controlling a plant disease, comprising applying the above mentioned agricultural or horticultural fungicide composition to a plant.

In the formula (I), the $C_{1-6}$ alkyl group or the alkyl moiety of the $C_{1-6}$ alkoxy group as represented by R includes an alkyl group having 1 to 6 carbon atoms, such as methyl, ethyl, propyl, butyl, pentyl or hexyl, which may have either a straight chain or a branched chain. When n is 2 or greater, the plural Rs are the same or different.

Examples of the imidazole compound represented by formula (I) include the following compounds:

4-chloro-2-cyano-1-dimethylsulfamoyl-5-(4-methylphenyl)imidazole (Compound No. 1);
4-chloro-2-cyano-1-dimethylsulfamoyl-5-(4-methoxyphenyl)imidazole (Compound No. 2);
4-chloro-2-cyano-1-dimethylsulfamoyl-5-(4-ethylphenyl)imidazole (Compound No. 3); and
4-chloro-2-cyano-1-dimethylsulfamoyl-5-(3-methyl-4-methoxyphenyl)imidazole (Compound No. 4).

The imidazole compounds represented by the above formula (I) can be prepared by the methods disclosed in EP-A-298196, EP-A-705823 and the like. In addition, Compound No. 1 is known as Cyazofamid in terms of a common name.

The polyoxins which is used as an active ingredient (b) of the present invention is a compound disclosed on pages 795-797 of *The Pesticide Manual* (Thirteenth Edition; BRITISH CROP PROTECTION COUNCIL, 2003). The polyoxins is not a single compound, but a complex comprising a series of compounds which resemble each other in chemical structure. The polyoxin mainly comprising polyoxin B and the polyoxin mainly comprising polyoxin D are used as a fungicide. In the present invention, both of them are applicable.

Since the agricultural or horticultural fungicide composition comprising (a) at least one imidazole compound represented by the above formula (I) and (b) polyoxins as active ingredients exhibits an excellent fungicidal activity by applying cultivated crops, for example, vegetables, such as cucumbers, tomatoes, and eggplants; cereals such as rice and wheat; peas; fruit trees, such as apples, pears, grapes and citrus; and potatoes, which are infected or have a possibility to be infected by harmful pathogens, it is desirable for controlling diseases such as powdery mildew, downy mildew, anthracnose, gray mold, common green mold, scab, alternaria blotch, bacterial blight, black spot, black spot disease, ripe rot, late blight, ring spot, blast, sheath blight, seedling blight and southern blight. In addition, the agricultural or horticultural fungicide composition of the present invention exhibits an excellent control effect against soil-borne diseases caused by plant pathogens, such as *Fusarium, Rhizoctonia, Verticillium, Plasmodiophora*, and *Pythium*. The agricultural or horticultural fungicide composition of the present invention has a long residual efficacy, an excellent penetration and translocation, and preventive and/or therapeutic effect and especially it is excellent in a preventive effect.

The agricultural or horticultural fungicide composition of the present invention exhibits a control effect against a disease, such as rice blast; rice sheath blight; rice seedling blight; cucumber anthracnose; downy mildew of cucumbers, melons, cabbages, Chinese cabbages, onions, pumpkins, and grapes; powdery mildew of wheat, barley, and cucumbers; blight of potatoes, red peppers, sweet peppers, watermelons, pumpkins, tobaccos, and tomatoes; wheat *Septoria* disease; tomato early blight; citrus melanose; citrus common green mold; pear scab; apple alternaria blotch; onion white tip; watermelon brown rot; diseases, such as various gray mold, crown rot, rust, and bacterial blight; and various soil-borne diseases caused by plant pathogenic fungi, such as *Fusarium, Pythium, Rhizoctonia,* and *Verticillium*. In addition, the agricultural or horticultural fungicide composition exhibits an excellent control effect against diseases caused by *Plasmodiophora*. More specifically, the composition exhibits an especially excellent control effect against diseases such as blight of potatoes, red peppers, sweet peppers, watermelons, pumpkins, tobaccos, and tomatoes; downy mildew of cucumbers, melons, cabbages, Chinese cabbages, onions, pumpkins, and grapes; and diseases of turf such as *Pythium* blight, *Pythium* red blight and *Rhizoctonia* rot (brown patch and large patch).

The active ingredients which constitute the agricultural or horticultural fungicide composition of the present invention can be formulated into a variety of forms, such as emulsifiable concentrates, dustable powders, wettable powders, soluble concentrates, granules, suspension concentrates, etc., together with various adjuvants, as in conventional agricultural preparations. The active ingredients, at least one imidazole compound of the above formula (I), and other specific compounds may be mixed and formulated, or each of them may be separately formulated and then mixed together. Upon use, the preparation may be used as such or as diluted with an appropriate diluent, e.g., water, to a predetermined concentration. Examples of the adjuvants which can be used include carriers, emulsifying agents, suspending agents, thickeners, stabilizers, dispersants, spreaders, wetting agents, penetrating agents, antifreezing agents, antifoaming agents and the like. These adjuvants are added appropriately, if necessary. The carriers are classified into solid carriers and liquid carriers. The solid carriers include animal and vegetable powders (e.g., starch, sugar, cellulose powders, cyclodextrin, activated charcoal, soybean powders, wheat powders, chaff powders, wood powders, fish powders, powdery milk, etc.); mineral powders (e.g., talc, kaolin, bentonite, organic bentonite, calcium carbonate, calcium sulfate, sodium hydrogencarbonate, zeolite, diatomaceous earth, white carbon, clay, alumina, silica, sulfur powder, slaked lime, etc.); and the like. Examples of the liquid carriers include water, vegetable oils (e.g., soybean oil, cotton seed oil, etc.), animal oils (e.g., beef tallow, whale oil, etc.), alcohols (e.g., ethyl alcohol, ethylene glycol, etc.), ketones (e.g., acetone, methyl ethyl ketone, methyl isobutyl ketone, isophorone, etc.), ethers (e.g., dioxane, tetrahydrofuran, etc.), aliphatic hydrocarbons (e.g., kerosene, lamp oil, liquid paraffin, etc.), aromatic hydrocarbons (e.g., toluene, xylene, trimethylbenzene, tetramethylbenzene, cyclohexane, solvent naphtha, etc.), halogenated hydrocarbons (e.g., chloroform, chlorobenzene, etc.), acid amides (e.g., dimethylformamide, etc.), esters (e.g., acetic acid ethyl ester, fatty acid glycerine esters, etc.), nitriles (e.g., acetonitrile, etc.), sulfur-containing compounds (e.g., dimethyl sulfoxide, etc.), N-methyl-2-pyrrolidone, N,N-dimethylformamide, N,N-dimethylacetamide, and the like. Examples of the spreaders include sodium alkylsulfate, sodium alkylbenzene sulfonate, sodium lignin sulfonate, polyoxyethylene glycol alkyl ether, polyoxyethylene lauryl ether, polyoxyethylene alkyl aryl ether, polyoxyethylene sorbitan fatty acid ester and the like.

In addition, in the method of the present invention, the agricultural or horticultural fungicide composition of the present invention can be mixed with other agricultural chemicals, such as a fungicide, an insecticide, a miticide, a nematocide, a soil insect pesticide, an antivirus agent, an attractant, a herbicide, a plant growth regulating agent and in this case, further excellent effect is exhibited in some cases.

The active ingredient compounds of the fungicide in the above-mentioned other agricultural chemicals include, for example, (by common names, some of them are still in an application stage):

anilinopyrimidinamine compounds, such as mepanipyrim, pyrimethanil, and cyprodinil;

pyridinamine compounds, such as fluazinam;

azole compounds, such as triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, sipconazole, prothioconazole, triadimenol, flutriafol, difenoconazole, fluquinconazole, fenbuconazole, bromuconazole, diniconazole, tricyclazole, probenazole, simeconazole, pefurazoate, ipconazole and imibenconazole;

quinoxaline compounds, such as quinomethionate;

dithiocarbamate compounds, such as maneb, zineb, mancozeb, polycarbamate, metiram, propineb and thiram;

organic chlorine compounds, such as fthalide, chlorothalonil and quintozene;

imidazole compounds, such as benomyl, thiophanate-methyl, carbendazim, thiabendazole and fuberidazole;

cyanoacetamide compounds, such as cymoxanil;

phenylamide compounds, such as metalaxyl, metalaxyl-M, mefenoxam, oxadixyl, ofurace, benalaxyl, benalaxyl-M (another name: kiralaxyl, chiralaxyl), furalaxyl, and cyprofuram;

sulfenic acid compounds, such as dichlofluanid;

copper compounds, such as cupric hydroxide and oxine copper;

isoxazole compounds, such as hymexazol;

organophosphorus compounds, such as fosetyl-Al, tolcofos-methyl, S-benzyl O,O-diisopropylphosphorothioate, O-ethyl S,S-diphenylphosphorodithioate, aluminum ethylhydrogen phosphonate, edifenphos, and iprobenfos;

N-halogenothioalkyl compounds, such as captan, captafol and folpet;

dicarboximide compounds, such as procymidone, iprodione and vinclozolin;

benzanilide compounds, such as flutolanil, mepronil, zoxamide and tiadinil;

anilide compounds, such as carboxin, oxycarboxin, thifluzamide, penthiopyrad, boscalid, bixafen, fluopyram and isotianil;

piperazine compounds, such as triforine;

pyridine compounds, such as pyrifenox;

carbinol compounds, such as fenarimol and flutriafol;

piperidine compounds, such as fenpropidine;

morpholine compounds, such as fenpropimorph, spiroxamine and tridemorph;

organotin compounds, such as fentin hydroxide and fentin acetate;

urea compounds, such as pencycuron;

cinnamic acid compounds, such as dimethomorph and flumorph;

phenylcarbamate compounds, such as diethofencarb;

cyanopyrrole compounds, such as fludioxonil and fenpiclonil;

strobilurin compounds, such as azoxystrobin, kresoxim-methyl, metominofen, trifloxystrobin, picoxystrobin, oryzastrobin, dimoxystrobin, pyraclostrobin, and fluoxastrobin;

oxazolidinone compounds, such as famoxadone;

thiazolecarboxamide compounds, such as ethaboxam;

silylamide compounds, such as silthiopham;

amino acid amide carbamate compounds, such as iprovalicarb, benthiavalicarb-isopropyl and valiphenal;

imidazolidine compounds, such as fenamidone;

hydroxyanilide compounds, such as fenhexamid;

benzenesulfonamide compounds, such as flusulfamid;

oxime ether compounds, such as cyflufenamid;

phenoxyamide compounds, such as fenoxanil;

anthraquinone compounds;

crotonic acid compounds;

antibiotics, such as validamycin, and kasugamycin;

guanidine compounds, such as iminoctadine;

and other compounds, such as pyribencarb, isoprothiolane, pyroquilon, diclomezine, quinoxyfen, propamocarb hydrochloride, chloropicrin, dazomet, metam-sodium, nicobifen, metrafenone, UBF-307, diclocymet, proquinazid, amisulbrom (another name: amibromdole), Syngenta 446510 (mandipropamid, dipromandamid), fluopicolide, carpropamid, BCF051, BCM061, BCM062, and AF-0201.

The active ingredient compounds of an insect pest control agents, such as the insecticide, the miticide, or the nematicide in the above-mentioned other agricultural chemicals, include, for example, (by common names, some of them are still in an application stage):

organic phosphate ester compounds, such as profenofos, dichlorvos, fenamiphos, fenitrothion, EPN, diazinon, chlorpyrifos-methyl, acephate, prothiofos, fosthiazate, phosphocarb, cadusafos, disulfoton, chlorpyrifos, demeton-S-methyl, dimethoate, methamidophos, imicyafos, isoxathion, isofenphos, ethion, etrimfos, quinalphos, dimethylvinphos, sulprofos, thiometon, vamidothion, pyraclofos, pyridaphenthion, pirimiphos-methyl, propaphos, phosalone, formothion, malathion, tetrachlorvinphos, chlorfenvinphos, cyanophos, trichlorfon, methidathion, phenthoate, ESP, azinphos-methyl, fenthion, heptenophos, methoxychlor, parathion, monocrotophos, parathion-methyl, terbufos, phosphamidon, phosmet and phorate;

carbamate compounds, such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC and fenothiocarb;

nereistoxin derivatives, such as cartap, thiocyclam, bensultap and thiosultap-sodium;

organic chlorine compounds, such as dicofol, tetradifon, endosulfan, dienochlor and dieldrin;

organic metal compounds, such as fenbutatin oxide and cyhexatin;

pyrethroid compounds, such as fenvalerate, permethrin, cypermethrin, deltamethrin, cyhalothrin, tefluthrin, ethofenprox, flufenprox, fenpropathrin, bifenthrin, imidate, cyfluthrin, flucythrinate, fluvalinate, cycloprothrin, lambda-cyhalothrin, pyrethrins, esfenvalerate, tetramethrin, resmethrin, protrifenbute, zeta-cypermethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, and metofluthrin;

benzoylurea compounds, such as diflubenzuron, chlorfluazuron, teflubenzuron, flufenoxuron, lufenuron, novaluron, triflumuron, hexaflumuron, bistrifluoron, noviflumuron and fluazuron;

juvenile hormone-like compounds, such as methoprene, pyriproxyfen, fenoxycarb and diofenolan;

pyridazinone compounds, such as pridaben;

pyrazole compounds, such as fenpyroximate, fipronil, tebufenpyrad, ethiprole, tolfenpyrad, acetoprole, pyrafluprole and pyriprole;

neonicotinoids, such as imidacloprid, nitenpyram, acetamiprid, thiacloprid, thiamethoxam, clothianidin, nidinotefuran, and dinotefuran;

hydrazine compounds, such as tebufenozide, methoxyfenozide, chromafenozide and halofenozide;

pyridine compounds, such as pyridaryl and flonicamid;

tetronic acid compounds, such as spirodiclofen;

strobilurin compounds, such as fluacrypyrin;

pyridinamine compounds, such as flufenerim;

dinitro compounds; organic sulfur compounds; urea compounds; triazine compounds; hydrazone compounds;

other compounds, such as buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, flufenerim, pyridalyl, spirodiclofen, bifenazate, spirotetramat, propargite, verbutin, spiromesifen, thiazolyl-cinnamonitrile, amidoflumet, flubendiamide, clofentezine, metaflumizone, chlorantraniliprole, HGW-86, cyflumetofen, cyenopyrafen, pyrifluquinazone, fenazaquin, pyridaben, amidoflumet, chlorobenzoate, sulfluramid, metaldehyde, and ryanodine; AKD-1022 and IKA-2000; and the like.

Further, it may be used in combination with or together with insecticidal crystal proteins produced by *Bacillus thuringienses aizawai, Bacillus thuringienses kurstaki, Bacillus thuringiensis israelenses, Bacillus thuringienses japonensis, Bacillus thuringienses tenebrionis*, or *Bacillus thuringienses*; microbial pesticide, such as insect viruses, entomopathogenic fungi, and nematophagous fungi; antibiotics, such as avermectin, milbemectin, milbemycin, spinosad, emamectin benzoate, ivermectin, lepimectin, spinetoram, abamectin, and emamectin; natural products, such as azadirachtin and rotenone; repellents, such as deet; and the like.

In the agricultural or horticultural fungicide composition of the present invention, a suitable weight ratio of (a) at least one imidazole compound of the formula (I) to (b) polyoxins is preferably a mixing ratio corresponding to an effective amount (a synergistic effective amount) of each ingredient which exhibits a synergistic effect when both of them are used in combination. The suitable weight ratio is usually from 1:10,000 to 10,000:1, preferably from 1:1,000 to 1,000:1, more preferably 1:100 to 100:1.

The present invention also relates to a method for controlling a plant disease comprising applying the agricultural or horticultural fungicide composition of the present invention to a plant. Concentration of the active ingredient to be used for the agricultural or horticultural fungicide composition of the present invention varies depending on differences in objective crops, use method, preparation form, application amount, application time, kinds of harmful pathogens and the like, and cannot necessarily be defined. However, in foliage treatment or soil-drenching treatment, as an active ingredient concentration, the imidazole compound of the above formula (I) is usually used in a concentration of from 0.01 to 1,000 ppm, preferably from 0.3 to 500 ppm, and the concentration of polyoxins is usually used in a concentration of from 0.1 to 10,000 ppm, preferably from 0.5 to 5,000 ppm.

Advantageous Effects of Invention

In the agricultural or horticultural fungicide composition of the present invention, the controlling effect against a cultivated crop infected by a plant pathogen is stable and highly active so that the composition can control a plant disease.

DESCRIPTION OF EMBODIMENTS

Next, preferable embodiments of the agricultural or horticultural fungicide composition of the present invention are exemplified, but the present invention should not be construed that the invention is limited to these embodiments.
(1) An agricultural or horticultural fungicide composition comprising (a) at least one imidazole compound represented by formula (I) and (b) polyoxins as active ingredients.
(2) The agricultural or horticultural fungicide composition described in the above (1), which comprises a synergistic effective amount of (a) at least one imidazole compound represented by formula (I) and (b) polyoxins.
(3) The agricultural or horticultural fungicide composition described in the above (1), wherein a weight ratio of (a) at least one imidazole compound represented by formula (I) to (b) polyoxins is 1:10,000 to 10,000:1.
(4) The agricultural or horticultural fungicide composition described in the above (1), wherein a weight ratio of (a) at least one imidazole compound represented by formula (I) to (b) polyoxins is 1:1,000 to 1,000:1.
(5) The agricultural or horticultural fungicide composition described in the above (1), wherein the imidazole compound represented by formula (I) is Cyazofamid.

EXAMPLES

Next, Test Examples with regard to the present invention described below, but the present invention should not be construed that the invention is limited to these Examples.

Test Example 1

Inhibition Test of Mycelial Growth Against Rice Seedling Blight (*Pythium spinosum*)

The strain to use for a test was precultured on a PSA plate for two days at 20° C. Then, the peripheral portion of the grown mycelia was cut out with a cork borer (4 mm in diameter) to put on PDA plate which was prepared to contain an active ingredient at a predetermined concentration by diluting. After culturing for two days at 20° C., a diameter of the mycelial colony was measured to obtain an inhibition rate of mycelial growth.

The result was shown in Table 1.

In addition, a theoretical value of the inhibition rate was calculated using Colby's formula and listed in parentheses of Table 1. If an experimental value is higher than a theoretical value obtained by Colby's formula, the agricultural or horticultural fungicide composition of the present invention exhibit a synergistic effect on controlling of a plant disease.

TABLE 1

| | Cyazofamid Inhibition Rate of Mycelial Growth against *Pythium spinosum* (%) (Theoretical Value) | | |
|---|---|---|---|
| | 10.0 ppm | 1.0 ppm | 0 ppm |
| Polyoxin complex mainly comprising polyoxin B 100 ppm | 88 (54) | 71 (68) | 0 |
| 0 ppm | 54 | 68 | |

Test Example 2

Inhibition Test of Mycelial Growth Against Turf *Pythium* Blight (*Pythium graminicola*)

The inhibition rate of mycelial growth was obtained by measuring mycelial growth in the same manner as Test Example 1. The result was shown in Table 2. In addition, the mean mycelial growth of non-treated group was 46.5 mm.

TABLE 2

| | Cyazofamid Inhibition Rate of Mycelial Growth (%) (Theoretical Value) | | | |
|---|---|---|---|---|
| Agent to be combined with | 100 | 10 | 1 | 0 ppm |
| Zinc salt of polyoxin D mainly comprising polyoxin D 100 ppm | 92 (83) | 90 (72) | 92 (73) | 48 |
| Polyoxin complex mainly comprising polyoxin B 100 ppm | 76 (68) | 74 (47) | 68 (48) | 0 |
| 0 ppm | 68 | 47 | 48 | 0 |

Next, examples of the harmful organism control composition of the present invention described below as Formulation Examples, but the present invention should not be construed that the invention is limited to these Examples.

Formulation Example 1

| (1) Cyazofamid | 2 parts by weight |
|---|---|
| (2) Polyoxin complex mainly comprising polyoxin B | 10 parts by weight |
| (3) Sodium naphthalene sulphonate formaldehyde condensates | 5 parts by weight |
| (4) Sodium alkyl benzene sulphonate | 5 parts by weight |
| (5) Clay | 78 parts by weight |

The foregoing each component is mixed to obtain a wettable powder.

Formulation Example 2

| (1) Cyazofamid | 0.5 parts by weight |
|---|---|
| (2) Polyoxin complex mainly comprising polyoxin B | 2.5 parts by weight |
| (3) Calcium carbonate | 20 parts by weight |
| (4) Clay | 77 parts by weight |

The foregoing each component is mixed to obtain a dustable powder.

While the invention has been described in detail and with reference to specific embodiments thereof, it will be apparent to one skill in the art that various changes and modifications can be made therein without departing from the sprit and scope thereof.

This application is based on Japanese patent application Nos. 2008-085318 and 2008-135649 filed on Mar. 28, 2008 and May 23, 2008, respectively, the entire contents of which are incorporated hereinto by reference. All references cited herein are incorporated in their entirety.

INDUSTRIAL APPLICABILITY

In the agricultural or horticultural fungicide composition of the present invention, the controlling effect against a cultivated crop infected by a plant disease is stable and highly active so that the composition can control a plant disease.

The invention claimed is:

1. An agricultural or horticultural fungicide composition, comprising (a) Cyazofamid, and (b) polyoxins as active ingredients, wherein the weight ratio of (a) Cyazofamid to (b) polyoxins is 1:100 to 100:1.

2. The agricultural or horticultural fungicide composition according to claim 1, wherein the composition comprises a synergistic effective amount of (a) Cyazofamid and (b) polyoxins.

3. A method for controlling a plant disease, comprising applying the agricultural or horticultural fungicide composition according to claim 1 to a plant.

4. A method for controlling a plant disease, comprising applying the agricultural or horticultural fungicide composition according to claim 2 to a plant.

5. The agricultural or horticultural fungicide composition according to claim 1, wherein the weight ratio of (a) cyazofamid to (b) polyoxins is 1:100 to 1:1.

6. The method for controlling a plant disease according to claim 3, wherein the composition is applied to a turf.

7. The method for controlling a plant disease according to claim 6, wherein the composition is applied to a turf.

* * * * *